(12) United States Patent
Nagy et al.

(10) Patent No.: US 7,396,931 B2
(45) Date of Patent: Jul. 8, 2008

(54) PROCESS FOR THE PREPARATION OF AMORPHOUS FORM OF A PLATELET AGGREGATION INHIBITOR DRUG

(75) Inventors: Péter Kótay Nagy, Vác (HU); Gyula Simig, Budapest (HU); József Barkóczy, Budapest (HU); Tamás Gregor, Csömör (HU); Béla Farkas, Veszprém (HU); Györgyi Vereczkeyné Donáth, Budapest (HU); Kálmán Nagy, Budapest (HU); Gyuláné Körtvélyessy, Budapest (HU); Zsuzsanna Szent-Királlyi, Budapest (HU)

(73) Assignee: Egis Gyógyszergyár Rt., Budapest (HU)

( * ) Notice: Subject to any disclaimer, the term of this patent is extended or adjusted under 35 U.S.C. 154(b) by 0 days.

(21) Appl. No.: 10/562,978

(22) PCT Filed: Jun. 30, 2004

(86) PCT No.: PCT/HU2004/000069

§ 371 (c)(1),
(2), (4) Date: Dec. 29, 2005

(87) PCT Pub. No.: WO2005/003138

PCT Pub. Date: Jan. 13, 2005

(65) Prior Publication Data

US 2007/0117837 A1    May 24, 2007

(30) Foreign Application Priority Data

Jul. 2, 2003  (HU) .................. 0302029
Jun. 23, 2004  (HU) .................. 0401269

(51) Int. Cl.
*C07D 471/02* (2006.01)

(52) U.S. Cl. ..................... 546/114

(58) Field of Classification Search ......... 546/232, 546/114
See application file for complete search history.

(56) References Cited

U.S. PATENT DOCUMENTS

| 4,847,265 A | 7/1989 | Badorc et al. |
| 2002/0198229 A1 | 12/2002 | Bousquet et al. |

FOREIGN PATENT DOCUMENTS

| EP | 281 459 | 9/1988 |
| FR | 98/07464 | 6/1998 |
| WO | WO 02/059087 | 8/2002 |
| WO | WO-02/059087 A1 | 8/2002 |
| WO | WO 02/059128 | 8/2002 |
| WO | WO 03/051362 | 6/2003 |
| WO | WO-03/051362 A | 6/2003 |
| WO | WO 03/051362 A2 * | 6/2003 |
| WO | WO-2004/081016 A | 9/2004 |

* cited by examiner

*Primary Examiner*—D. Margaret Seaman
*Assistant Examiner*—Nizal S Chandrakumar
(74) *Attorney, Agent, or Firm*—Birch, Stewart, Kolasch & Birch, LLP

(57) ABSTRACT

The present invention relates to a new method of preparation of the polymorph form 1 of methyl (S)-(+)-(2-chlorophenyl)-2-(6,7-dihydro-4H-thieno[3,2-c]pyridine-5-yl-acetate hydrogensulfate of the formula (I)

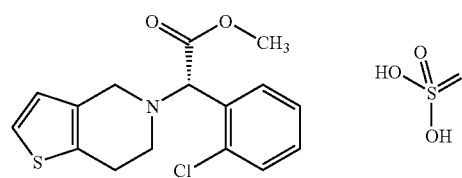

8 Claims, No Drawings

PROCESS FOR THE PREPARATION OF AMORPHOUS FORM OF A PLATELET AGGREGATION INHIBITOR DRUG

The present invention relates to a new method for the preparation of the amorphous form of methyl (S)-(+)-(2-chlorophenyl)-2-(6,7-dihydro-4H-thieno[3,2-c]pyridine-5-yl-acetate hydrogensulfate of the Formula

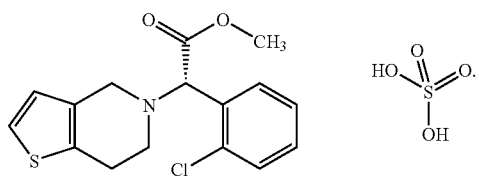

I

TECHNICAL BACKGROUND OF THE INVENTION (S)-(+)-(2-chlorophenyl)-2-(6,7-dihydro-4H-thieno[3,2-c]pyridine-5-yl-acetate hydrogensuifate is a known platelet aggregation inhibitor drug, having INN clopidogrel hydrogensulfate.

Clopidogrel hydrogensulfate is described first in European Patent Specification No. 281 459. Hungarian equivalent of this patent is Hungarian patent No. 197 909.

The product is characterized by its melting point and optical rotation, which are 182° C. and $[\alpha]_D^{20}=+51.61$ (c=2.044 g/100 ml, methanol) respectively. Crystal form of the product is not mentioned.

Polymorph forms of clopidogrel hydrogensulfate are described first in the French Patent Application No. 98/07464. Polymorph form 1 is specified as a monocline crystal form, characterized by X-ray diffraction pattern and infrared spectrum.

Melting point and the optical rotation of the form 1 are 184° C. and $[\alpha]_D^{20}=+55.1°$ (c=1.891/100 ml, methanol respectively. On the basis of these data, authors state that the polymorph form described in the European patent specification No. 281 459 is identical to polymorph form 1. The orthorhombic polymorph form 2 is characterized by its melting point of 176° C. in the specification of French Patent Application No. 98/07464.

Polymorph form 1 is prepared according to cited specification by dissolving clopidogrel base in acetone and adding 80% sulfuric acid in an equimolecular amount to the solution at 20° C. The solvent is evaporated partly, the residue is cooled to 0-5° C. and the precipitate is filtered.

Polymorph form 2 is precipitated out of the filtrate, which is obtained in the process of the preparation of polymorph form 1 and stored for 3-6 months below 40° C.

According to this patent specification, polymorph form 2 can also be prepared by adding equimolar amount of 80% sulfuric acid to a solution of clopidogrel base in acetone at 20° C. without or in the presence of seeding crystals. Subsequently the reaction mixture is boiled for two hours, the solvent is evaporated partly, the residue is cooled to −5° C., and either the precipitated product is filtered, or seeding crystals are added, the reaction mixture is stirred at 20° C., then the product is filtered.

According to the specification of the International Patent Application No. 02/059128, polymorph form 1 of clopiodogrel hydrogensulfate is prepared by the reaction of the solution of clopidogrel sulfate in threefold amount of acetone calculated based on the amount of clopidogrel base with concentrated sulfuric acid between 0-5° C. After addition of sulfuric acid, one more part of acetone is added, then the reaction mixture is stirred for 4 hours. Then polymorph form 1 is isolated with a melting point of 185° C.

According to the specification of International Patent Application No. 03/051362, amorphous form or several polymorph forms of clopidogrel hydrogensulfate are obtained by recrystallisation of clopidogrel hydrogensulfate using different solvents, or by the precipitation with anti-solvents from its solutions.

Amorphous clopidogrel hydrogensulfate is prepared according to International Patent Application No. 03/051362 by dissolution of clopidogrel hydrogen sulfate in methanol or ethanol, then to the obtained solution are diethyl ether or methyl tert-butyl ether added, the solubility of clopidogrel hydrogensulfate is reduced in the mixture and clopidogrel hydrogensulfate is precipitated out of the solution in amorphous form.

In another case, solution of clopidogrel hydrogensulfate in ethanol is added to boiling toluene, then the solution is cooled, yielding the amorphous product. The disadvantage of this process is the use of toluene being an aromatic solvent which is avoidable in the synthesis of a pharmaceutical drug, especially in the last step of the process.

In case of using an ether type solvent to precipitate out the product from its solution prepared in an alcohol or acetone, polymorph form 1 or amorphous form is formed according to the reaction conditions.

Moreover, the mixture of the amorphous and polymorph form 1 can be produced as well. In presence of ether type solvents, the amorphous product can be converted into polymorph form 1. Examples of the International Patent specification No. 03/051362 demonstrate the strong tendency of clopidogrel hydrogensulfate to crystallise.

Data summarised in the Table 1 demonstrate that the precipitation of clopidogrel hydrogensulfate results in different crystalline polymorph forms.

TABLE 1

| Solvent | Antisolvent | Morphology |
| --- | --- | --- |
| Acetonitrile | DEE | Polymorph form 2 |
| methanol | DEE | Amorphous |
| ethanol | MTBE or DEE | Polymorph form 1 |
| methanol | MTBE or DEE | Polymorph form 1 |
| ethanol | MTBE | Polymorph form 1 + Amorphous |
| methanol | DEE | Polymorph form 1 |
| 2-butanol | MTBE | Polymorph form 5 |

DEE: diethyl ether
MTBE: methyl-tert.-butyl ether

According to the Table 2, further polymorph forms are formed by triturating the evaporated residue of a solution of clopidogrel hydrogensulfate with solvents in which the solubility of clopidogrel hydrogen sulfate is very low or the product is immiscible with.

TABLE 2

| Solution | Solvent used for trituration | Morphology |
| --- | --- | --- |
| 1-butanol | DEE or MTBE | Polymorph form 3 |
| 2-butanol | DEE or MTBE | Polymorph form 5 |

TABLE 2-continued

| Solution | Solvent used for trituration | Morphology |
|---|---|---|
| 1-propanol | MTBE | Polymorph form 6 |
| Acetone | — | Amorphous |

DEE: diethyl ether
MTBE: methyl-tert.-butyl ether

The polymorph forms of the evaporated residues before the trituration are not mentioned in the specification. Although the amorphous form of clopidogrel hydrogensulfate can be produced by evaporation of the solution of clopidogrel hydrogensulfate in acetone to dryness, the process can not be accomplished easily on industrial scale.

It can not be predicted whether the amorphous product obtained after trituration in a suitable solvent remains amorphous form, since it may easily transform into different polymorphous forms spontaneously, for example into polymorph form 1.

According to the examples above, it is impossible to predict which polymorph form will be precipitated or transformed into other form by the interaction of clopidogrel hydrogensulfate and a selected solvent.

It is very important that the amorphous form can be changed into polymorph form 1 by triturating with ethers. In the same process, the trituration with ether results the polymorph form 2, while in other cases, polymorph forms depicted in Table 2 are formed.

Official requirements defined in Pharmacopoeias are ever increasing with regard to the purity and morphological uniformity of pharmaceutical active ingredients. Requirements towards morphological uniformity of a substance are justified by the fact that biological availabilities of different polymorph forms may be different.

According to the International Patent Application No 02/59087, the solubility and the biological availability of the amorphous form of the active agent having INN name atorvastatine calcium is better then its morphologically uniform crystalline forms.

Properties of different polymorph forms may be different from the pharmaceutical technology point of view. The use of amorphous form can be advantageous either from the economical or the technological point of view as well.

FIELD OF THE INVENTION

Therefore there is a long-felt need for developing a reproducible process for the preparation of stable amorphous form of methyl (S)-(+)-(2-chlorophenyl)-2-(6,7-dihydro-4H-thieno[3,2-c]pyridine-5-yl-acetate hydrogensulfate which meets the requirements for the pharmaceutically active agents specified in Pharmacopoeia.

Our aim is to provide a new process, which allows the use of different solvent types to produce the clopidogrel hydrogensulfate in amorphous form on an industrial scale reproducibly.

SUMMARY OF THE INVENTION

The present invention relates to a new process for the preparation of the amorphous form of methyl (S)-(+)-(2-chlorophenyl)-2-(6,7-dihydro-4H-thieno[3,2-c]pyridine-5-yl-acetate hydrogensulfate of the Formula (I) which comprises dissolving clopidogrel base in an "A" type solvent, adding sulfuric acid or a mixture of sulfuric acid with an "A" or "B" type solvent to the mixture, adding the obtained mixture containing clopidogrel hydrogensulfate to a "B" type solvent, and subsequently filtering, optionally washing and drying the obtained precipitate.

The basis of our invention is the recognition that when the solution of clopidogrel hydrogensulfate in a suitable solvent is mixed with another suitable solvent and worked up under appropriate circumstances, stable and pure amorphous form of clopidogrel hydrogensulfate is formed in a reproducible way.

We found surprisingly that use of dipolar aprotic solvents except acetonitrile instead of protic solvents as "A" type solvents results in the formation of stable amorphous product using different "B" type solvents.

It is known that different polymorph forms are precipitated out during the change of the polarity of the solutions containing clopidogrel hydrogensulfate depending on the solvents used. It is surprising that the technical solution we found for the preparation of clopidogrel hydrogensulfate in amorphous form is reproducible and industrially applicable procedure using different types of solvents.

DETAILED DESCRIPTION OF THE INVENTION

According to the present invention, less polar aprotic or dipolar aprotic solvents can be used as "A" type solvents. Halogenated solvents, preferably aliphatic halogenated solvents, more preferably dichloromethane can be used as less polar aprotic solvent.

Ketones, preferably lower aliphatic ketones, more preferably acetone can be used as dipolar aprotic solvent.

According to the process of the present invention, apolar or dipolar aprotic solvents can be used as "B" type solvents.

Ethers, aliphatic esters or saturated hydrocarbons are used as apolar solvents. Diethyl ether, tetrahydrofurane diisopropyl ether, preferably diisopropyl ether can be used as ether. Lower aliphatic esters preferably ethyl acetate can be used as dipolar aprotic solvent. Preferably hexane, cyclohexane or heptane can be used as saturated hydrocarbon.

The amorphous form can be prepared in a favourable manner on an industrial scale as well in a reproducible way according to our invention.

Great advantage of the present invention is that the solvents used can be chosen from more types of solvents than it would be possible according to the state of the art, and the chosen solvents can be adapted easily to the technology used to prepare the amorphous form of the clopidogrel hydrogensulfate in a reproducible process.

For example, the use of dichloromethane as "A" type solvent is very advantageous because after setting free clopidogrel base from its camphorsulphonic acid salt, the obtained base can be extracted with dichloromethane, and according to the present invention, clopidogrel hydrogensulfate can be obtained in amorphous form in one step without exchange of the solvent. Thus, required time and costs of chemicals are reduced as well.

Further details are described below without the limitation of the scope of the present invention to the examples.

EXAMPLE 1

Clopidogrel Hydrogensulfate Amorphous Form

A solution containing 32.2 g of clopidogrel base in 130 ml of acetone is stirred and cooled to between 10-15° C. then 10.2 g of 96 w/w % sulfuric acid are added. The obtained mixture is added to 1000 ml of diisopropyl ether dropwise at 0° C. in 15-20 minutes under stirring. Then the reaction mixture is stirred for an additional hour at 0° C., filtered, the precipitate is washed with 2×100 ml of cold diisopropyl ether.

Thus, 38 g (90.5%) of clopidogrel hydrogensulfate amorphous form are obtained.

$^1$H-NMR (DMSO-d$_6$, i400): 7.88 (d, J=6.5 Hz, 1H), 7.64 (dd, J1=1.8 Hz, J1=7.9 Hz 1H), 7.52 (m, 2H), 7.42 (d, J=5.1 Hz, 1H), 6.87 (d, J=5.1 Hz, 1H), 5.57 (b, 1H), 4.20 (b, 4.H), 3.74 (s, 3H), 3.08 (b, 2H). $^{13}$C-NMR: 167.65, 134.38, 132.07, 131.89, 130.74, 128.46, 125.67, 124.92, 65.77, 53.57, 50.27, 48.86, 22.6.

EXAMPLE 2

Clopidogrel Hydrogensulfate Amorphous Form

A solution containing 32.2 g of clopidogrel base in 200 ml of dichloromethane is stirred and cooled to 0° C., then 9.7 g of 96 w/w % sulfuric acid are added. The mixture is added to 850 ml of diisopropyl ether dropwise at 0° C. in 15-20 minutes under stirring.

The reaction mixture is stirred for an additional hour at 0° C., filtered, the precipitate is washed with 2×100 ml of cold diisopropyl ether, then dried.

Thus, 37 g (88.1%) of amorphous clopidogrel hydrogensulfate are obtained.

$^1$H-NMR (DMSO-d$_6$, i400): 7.88 (d, J=6.5 Hz, 1H), 7.64 (dd, J1=1.8 Hz, J1=7.9 Hz 1H), 7.52 (m, 2H, 7.42 (d, J=5.1 Hz, 1H), 6.87 (d, J=5.1 Hz, 1H), 5.57 (b, 1H), 4.20 (b, 4H), 3.74 (s, 3H), 3.08 (b, 2H).

$^{13}$C-NMR: 167.65, 134.38, 132.07, 131.89, 130.74, 128.46, 125.67, 124.92, 65.77, 53.57, 50.27, 48.86, 22.61.

EXAMPLE 3

Clopidogrel Hydrogensulfate Amorphous Form

A solution containing 32.2 g of clopidogrel base in 200 ml of dichloromethane is stirred and cooled in a bath containing ice, water and sodium chloride, then 10.2 g of 96 w/w % sulfuric acid are added. The solution is added to 800 ml of cyclohexane dropwise at 5-10° C. in 5 minutes under stirring. The reaction mixture is stirred for an additional hour, filtered, the precipitate is washed with 2×100 ml of cold cyclohexane, then dried for five days at room temperature.

Thus, 38.9 g (92.8%) of amorphous clopidogrel hydrogensulfate are obtained.

$^1$H-NMR (DMSO-d$_6$, i400): 7.88 (d, J=6.5 Hz, 1H), 7.64 (dd, J1=1.8 Hz, J1=7.9 Hz 1H), 7.52 (m, 2H), 7.42 (d, J=5.1 Hz, 1H), 6.87 (d, J=5.1 Hz, 1H), 5.57 (b, 1H), 4.20 (b, 4H), 3.74 (s, 3H), 3.08 (b, 2H).

$^{13}$C-NMR: 167.65, 134.38, 132.07, 131.89, 130.74, 128.46, 125.67, 124.92, 65.77, 53.57, 50.27, 48.86, 22.61.

EXAMPLE 4

Clopidogrel Hydrogensulfate Amorphous Form

A solution containing 32.2 g of clopidogrel base in 200 ml of dichloromethane is stirred, 10.2 g of 96 w/w % sulfuric acid are added at room temperature. The mixture is added to 1000 ml of ethyl acetate dropwise at 0° C. under stirring in 5 minutes. Then the reaction mixture is stirred for additional one hour, filtered, the amorphous precipitate is washed with 2×100 ml of cold ethyl acetate, then dried.

Thus, 34.37 g (82%) of clopidogrel hydrogensulfate amorphous form are obtained.

$^1$H-NMR DMSO-d$_6$, i400): 7.88 (d, J=6.5 Hz, 1H), 7.64 (dd, J1=1.8 Hz, J1=7.9 Hz 1H), 7.52 (m, 2H), 7.42 (d, J=5.1 Hz, 1H), 6.87 (d, J=5.1 Hz, 1H), 5.57 (b, 1H), 4.20 (b, 4H), 3.74 (s, 3H), 3.08 (b, 2H).

$^{13}$C-NMR: 167.65, 134.38, 132.07, 131.89, 130.74, 128.46, 125.67, 124.92, 65.77, 53.57, 50.27, 48.86, 22.61.

What we claim is:

1. Process for the preparation of the amorphous form of methyl (S)-(+)-(2-clolophenyl-2(6,7-dihydro-4H-thieno[3,2-c]pyridine-5-yl-acetate hydrogen-sulfate of the formula (I)

which comprises,
dissolving clopidogrel base in a first solvent,
adding sulfuric acid,
adding the obtained mixture containing clopidogrel hydrogensulfate to a second solvent to obtain a precipitate, and filtering precipitate,
wherein the first solvent and the second solvent are present in one of the following combinations selected from the group consisting of:
combination (i) acetone and diisopropyl ether;
combination (ii) dichloromethane and diisopropyl ether;
combination (iii) dichloromethane and cyclohexane; and
combination (iv) dichloromethane and ethyl acetate.

2. The process according to claim 1, wherein the method comprises:
dissolving clopidogrel base in dichloromethane to make a solution,
adding sulfuric acid to the solution,
mixing the solution with cyclohexane to form a precipitate, and
filtering the precipitate.

3. The process according to claim 1, which further comprises:
washing the precipitate; and
drying the precipitate.

4. The process according to claim 1, wherein the first solvent and the second solvent are present in combination (i) which is acetone and diisopropyl ether.

5. The process according to claim 1, wherein the first solvent and the second solvent are present in combination (ii) which is dichloromethane and diisopropyl ether.

6. The process according to claim 1, wherein the first solvent and the second solvent are present in combination (iv) which is dichloromethane and ethyl acetate.

7. The process according to claim 1, wherein said first solvent is present in an amount not greater than 37 ml per gram of clopidogrel base.

8. The process according to claim 1, wherein said first solvent is present in an amount of between 31 and 37 ml per gram of clopidogrel base.

* * * * *